United States Patent [19]

Chaudhuri

[11] 4,253,913
[45] Mar. 3, 1981

[54] METHOD FOR DETERMINING THE SURFACE ABRASIVENESS OF A PAPER MACHINE WEB

[75] Inventor: Partha S. Chaudhuri, Covington, Va.

[73] Assignee: Westvaco Corporation, New York, N.Y.

[21] Appl. No.: 41,988

[22] Filed: May 24, 1979

Related U.S. Application Data

[62] Division of Ser. No. 924,949, Jul. 17, 1978, Pat. No. 4,169,756.

[51] Int. Cl.³ .................. G01N 3/56; G01N 19/02
[52] U.S. Cl. .................................. 162/198; 73/7; 73/159; 116/208; 340/652
[58] Field of Search .................. 73/7, 159; 116/208; 340/52 A, 52 B, 652; 162/198, 263, DIG. 10; 364/471

[56] References Cited

U.S. PATENT DOCUMENTS

| | | | |
|---|---|---|---|
| 2,976,716 | 3/1961 | DeHaven | 73/7 |
| 3,216,238 | 11/1965 | Bailey | 73/7 |
| 3,456,236 | 7/1969 | Labartino et al. | 340/52 A |
| 3,805,228 | 4/1974 | Peeples | 340/52 A |
| 3,827,281 | 8/1974 | Hanel | 73/7 |
| 4,019,066 | 10/1979 | Lucas et al. | 162/DIG. 10 |

FOREIGN PATENT DOCUMENTS

760621 6/1967 Canada .................................. 73/159
2535396 2/1977 Fed. Rep. of Germany .......... 116/208

OTHER PUBLICATIONS

Power; "Machinable Plastic Laminates", *TAPPI*, vol. 57, No. 2, Feb. 1974, p. 95.
Power et al.; "Machinability Defects in Laminates Caused by Tool Wear", *Forest Products Journal*, vol. 24, No. 1, Jun. 1974, p. 40.
"Development of a Method for Evaluating the Relative Abrasiveness of Corrugating Medium," Inst. of Paper Chemistry Project 2696–18, Oct. 5, 1976.
McMahon, "A Portable Abrasiveness Tester for Corrugating Medium," *TAPPI*, Nov. 1978, p. 83.

*Primary Examiner*—S. Leon Bashore
*Assistant Examiner*—Steve Alvo
*Attorney, Agent, or Firm*—W. Allen Marcontell; Richard L. Schmalz

[57] ABSTRACT

A method and apparatus is described for obtaining a quantitative indication of paper web abrasiveness as the web subject of the test is in transit through the production machine. Test specimens of thin, sheet metal shim stock are held in light bearing pressure contact against the dry, finished or nearly finished web for a measured increment of web length. The measured quantity of specimen material lost to the measured quantity of passing web will yield a quotient indicative of the relative abrasiveness of the subject web.

3 Claims, 8 Drawing Figures

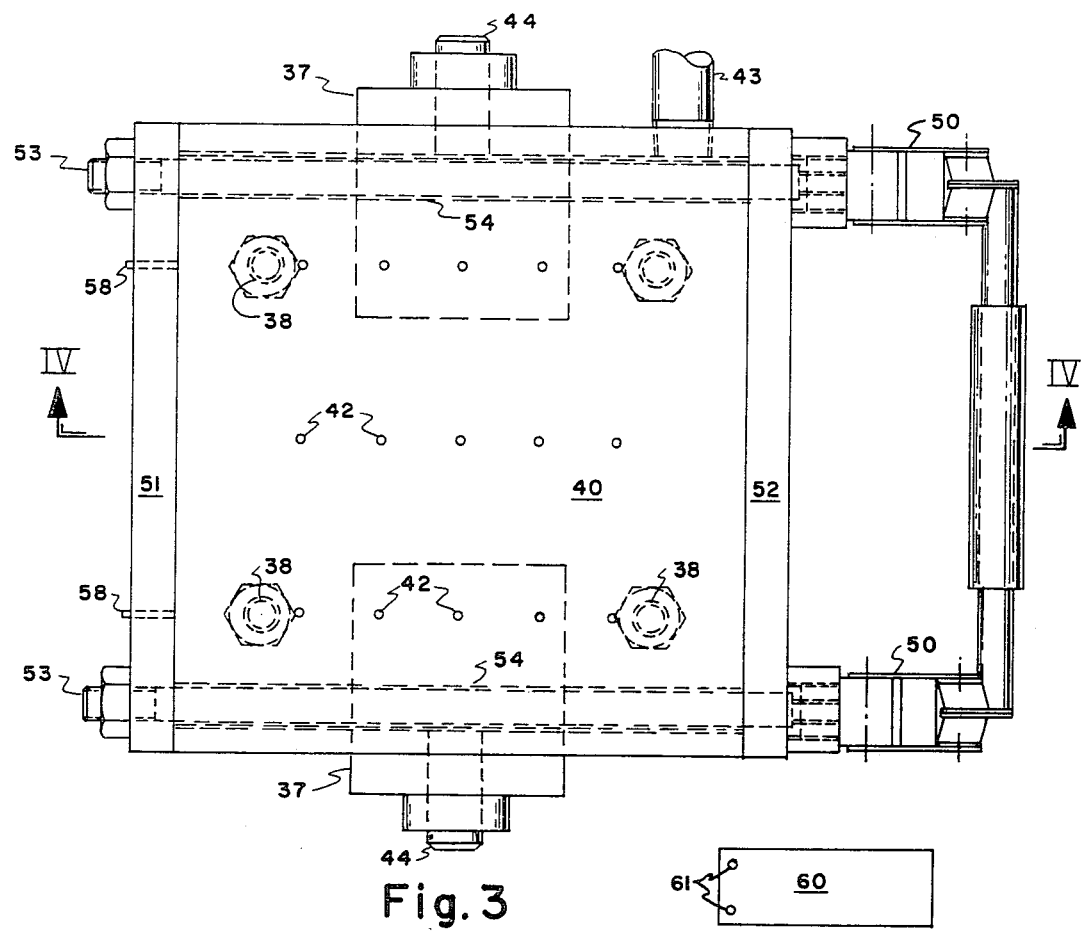
Fig. 3
Fig. 5
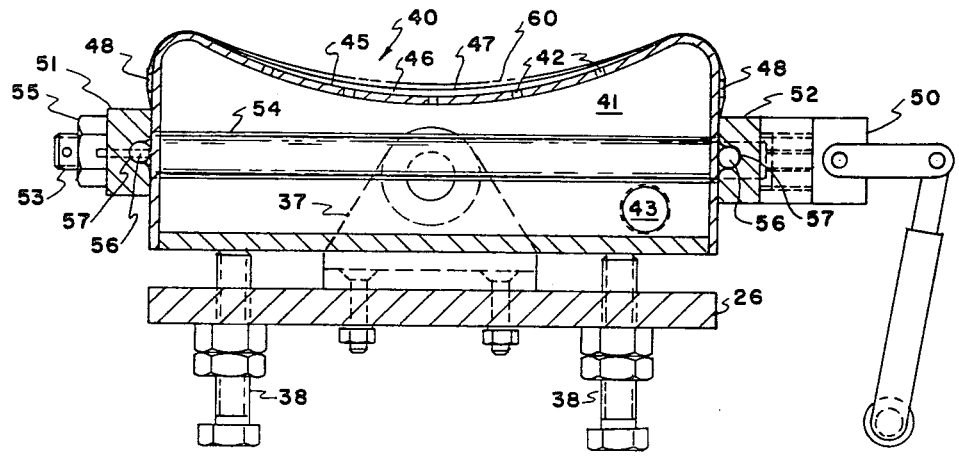
Fig. 4

METHOD FOR DETERMINING THE SURFACE ABRASIVENESS OF A PAPER MACHINE WEB

This is a division of application Ser. No. 924,949, filed July 17, 1978, now U.S. Pat. No. 4,169,756.

BACKGROUND OF THE INVENTION

1. Field of the Invention

The present invention relates to the art of papermaking and more particularly, to techniques for quantitatively monitoring the web characteristic of abrasiveness.

2. Description of the Prior Art

There are many paper converting operations having a high degree of sensitivity to the abrasive characteristic of paper. For example, decorative laminates made with multiple layers of phenolic impregnated kraft paper are machined to final shape with steel cutting tools which may be rapidly dulled. Another example is corrugating medium which abrades away the flutes of corrugating rolls in the primary manufacturing step of corrugated board.

These, and other manufacturing difficulties arising from paper abrasiveness are noted in detail by the publications of George E. Power found in TAPPI Vol. 57, No. 2, February, 1974 at page 95 and Forest Products Journal Vol. 24, No. 1, January, 1974 at page 40.

The abrasive characteristic of paper is due to the silica content thereof. Such silica originates as sand, grit and clay contaminates combined with the raw wood furnish from which the paper pulp is made. The caustic wood digestion process has little or no effect on the contaminates and once combined in the pulp flow stream are extremely difficult to remove. By additional processing such as multiple passes through centrifugal cleaners, such silica content may be significantly reduced. However, it would be prohibitive to process all the pulp produced by a typical two hundred and fifty ton per day pulp mill through cascades of centrifugal cleaners. Moreover, in any given pulp mill, an excessive presence of silica recurs only sporadically. Consequently, tests have been developed by the trade to quantify the abrasive result of silica contained in paper.

The most widely accepted paper abrasiveness test was developed by The Institute Of Paper Chemistry in Appleton, Wisconsin and reported in a paper of restricted dissemination for Project 2696-18 dated Oct. 5, 1976. Basically, this test involves the use of accurately weighed metal foil specimens (brass and steel) attached to the surface of a rotationally fixed cylinder. Over this foil clad cylinder at an approximately 170° wrap angle is drawn a two thousand foot length of twelve inch wide paper web sample. Such drawing is performed at a carefully controlled tensile force. Upon traverse of the sample length, the foil specimen is removed and weighed again for determination of material loss. The magnitude of such weight loss is directly attributed to the abrasiveness of the paper sample.

Although the results of this abrasiveness test are widely accepted as accurate and reliable, it will be noted that elaborate laboratory fixtures are required for an off-machine test having the inherent disadvantage of long delay times between the moment of web issue from the production machine and identification of a characteristic which ultimately relates back to the pulp from which the paper web was laid.

To rectify or at least reduce this informational hiatus, what is needed by the industry is an on-line test of the paper web as it is being formed to determine immediately if the abrasive quality of the paper so produced is increasing so that timely corrective measures may be taken.

It is therefore, an object of the present invention to teach a test procedure for determination of abrasive quality and an apparatus for conveniently performing such a test quickly while the web is still within the papermachine.

SUMMARY OF THE INVENTION

To accomplish these and other objectives, the present invention comprises an apparatus for engaging an accurately weighed metallic sheet specimen with the dry, finished, or nearly finished paper web still within the producing papermachine. Such engagement is directed, with a carefully regulated bearing pressure, radially against one of the several web turning rolls following the machine dryer section.

The present apparatus also comprises a calibrated wheel linear counter to record the actual length of web passing contact with the specimen.

Upon passage of a desired production length of web in contact with the initially weighed specimen, the specimen is withdrawn and removed from the apparatus for final weighing. The weight loss difference between the initial and final specimen weights is apportioned to the total web length or area having passing contact with the specimen to derive an abrasiveness index value.

Although the final measurement of a complete test is performed off-machine, the weighing apparatus required for such final test is small and relatively inexpensive, thereby permitting the weighing apparatus to be located in the immediate proximity of the subject papermachine. Consequently, the informational objective of the test may be known within a few minutes or before a reel of finished paper is completed.

Apparatus refinements may include automatic controls to disengage the specimen from test contact with the web upon arrival at a predetermined web test length. Additionally, the apparatus may be coordinated to the papermachine operation by a signal from the web-break alarm system to temporarily withdraw the specimen from test engagement upon occurrence of a web break and to re-engage the specimen upon restoration of web continuity without loss of the test length count.

BRIEF DESCRIPTION OF THE DRAWING

Relative to the drawing wherein like or similar reference characters used throughout the several figures of the drawing designate like or similar elements:

FIG. 3 is a plan view of the specimen support shoe for the present invention;

FIG. 4 is a sectional view of the specimen support shoe as taken along cut lines IV—IV of FIG. 3;

FIG. 5 is a plan view of the specimen sheet;

DESCRIPTION OF THE PREFERRED EMBODIMENT

Figure 1:
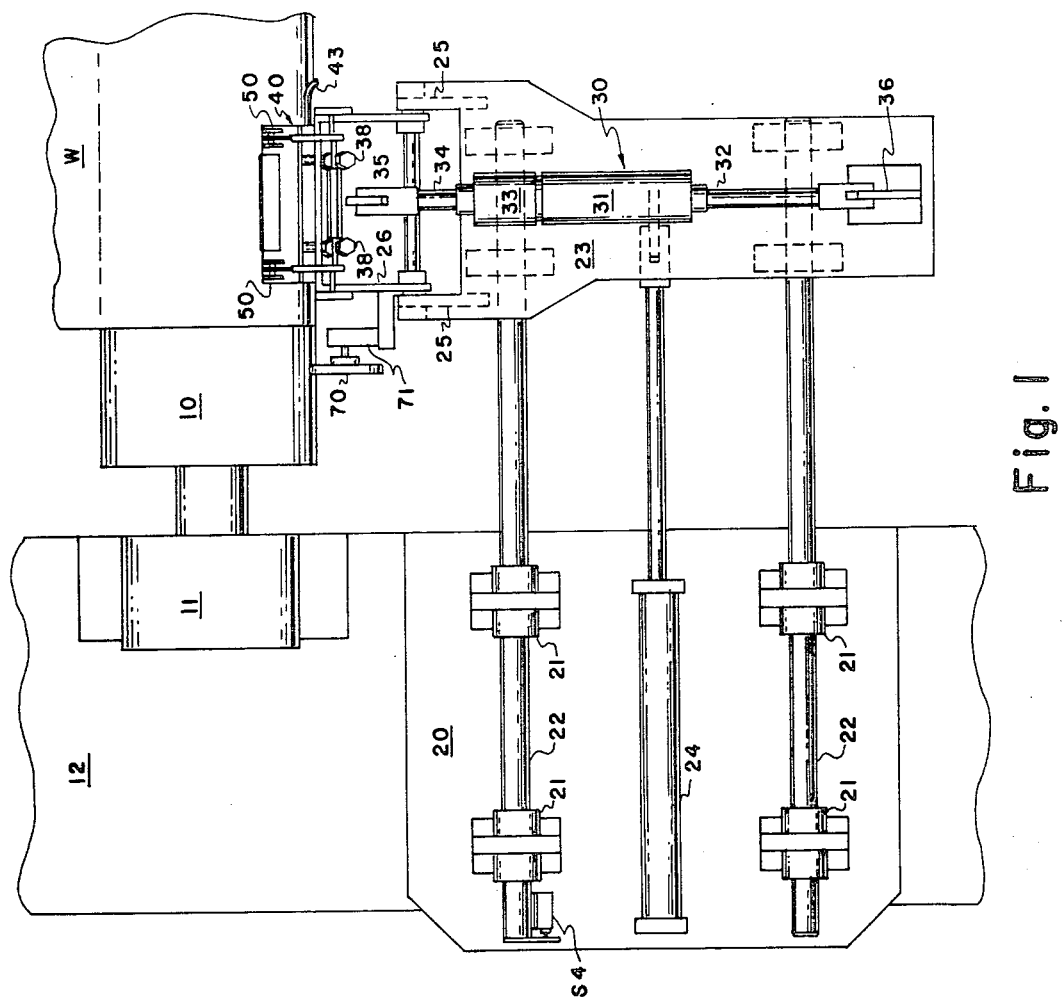
FIG. 1 is a front elevational view of the present apparatus mounted in operative position on the papermachine support frame.
Figure 2:
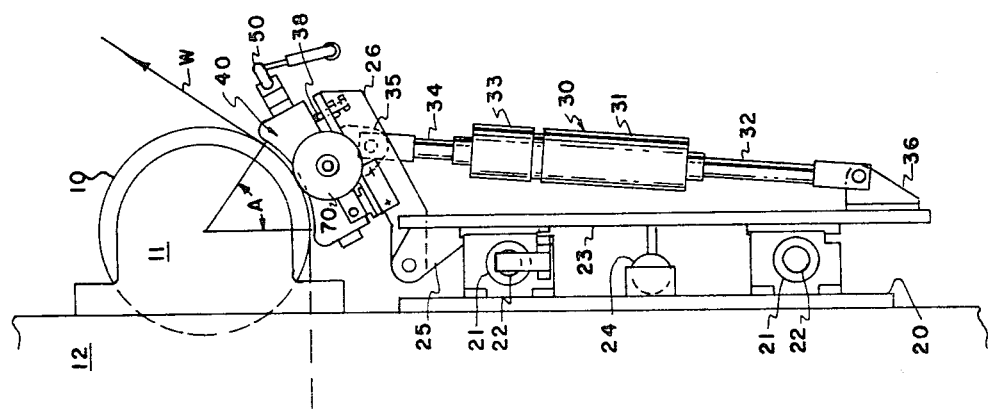
FIG. 2 is an end elevational view of the present invention.

Relative to FIGS. 1 and 2 there is shown an end portion of a turning roll 10 within the dry end section of a papermachine. Said turning roll 10 is secured at the ends thereof by journal bearings 11 mounted on a primary machine support frame column 12. The dry paper web W is coursed over an angular portion A of the turning roll 10 as the web traveling direction is changed along the undulating web route through the papermachine.

As a convenient mounting point, the present invention is secured to said frame column 12 by means of a base plate 20. To the base plate are mounted four linear bearings 21 which carry a pair of guide rods 22. Jointly, the guide rods carry a carriage platform 23. Between the base plate 20 and the carriage platform 23, a fluid cylinder motor 24 is secured by clevis joints to displace the carriage platform 23 between an extended position, as illustrated, and a retracted position.

Connected to the carriage platform 23 by mounting lugs 25 is a pivot bracket 26. This bracket 26 is driven through an angular arc between engagement and disengagement positions by a second fluid motor 30 connected between clevis lugs 35 on the pivot bracket 26 and clevis lugs 36 on the carriage platform 23.

Fluid motor 30 is comprised of two cylinder/strut sections 31/32 and 33/34. Cylinder 31 is the larger of the two and has a displaced volume and strut stroke approximately five times greater than cylinder 33.

Pivot bracket 26 is provided with two journal lugs 37 (FIGS. 3 and 4) secured to the upper bracket face by machine screws arranged to receive spacing shims between the bracket face and the respective lug bases.

The test shoe assembly 40, best illustrated by FIGS. 3 and 4, is basically a hollow housing 41 constituting an air plenum for cooling air discharge orifices 42. Air is supplied from an appropriate source by means of conduit 43. To the housing sides are secured journal rods 44 in cooperative alignment with lugs 37. Locking jack screws 38 threaded through the pivot bracket face secure an angular position of the shoe assembly 40 about the axis of journal rods 44.

The saddle face 45 of the shoe assembly is arced by a radius less than the cooperative turning roll 10 radius so as to provide a mid-space gap 46 between the saddle face 45 and a thin (0.015 inch) spring steel shim plate 47. Both ends of the shim plate 47 are secured to respective ends of assembly housing 41 by clamping bars 48.

To secure a test specimen 60 in position on the shoe 40 for the duration of a test interim, a specimen clamping assembly is provided having clamping bars 51 and 52 disposed across opposite housing ends. Such clamp bars 51 and 52 are tied together by a pair of clamp rods 53 extended through the housing 41 plenum within sealing channels 54. A nut 55 secures the clamping bar 51 to the rod 53 at one end thereof whereas a toggle-type compression clamp 50 secures the clamping bar 52 at the other end of the rod 53.

Between the rods 53 along the end faces of the housing 41 are provided crimping rods 56. A corresponding channel 57 is cut along the clamping face of clamp bars 51 and 52.

From the rotationally leading end face of housing 41 (relative to the rotational direction of turning roll 10) specimen alignment rods 58 projecting from the center of crimping rod 56 are provided. The FIG. 5 plan illustration of a representative specimen 60 in the new, uncrimped condition show apertures 61 punched into the face of the specimen of cooperative size and span to receive the alignment rods 58.

Most shim stock grades of sheet steel, copper and brass are suitable as test specimens 60 although the softer materials are preferred due to the greater quantity of base material abraded away per unit of linear contact with the running web W thereby reducing the elapsed test time. One particularly useful specimen 60 construction has been to electroplate 5 mil yellow brass shim stock with a half-mil cladding of copper. The visual contrast arising from the abraded removal of portions of the copper, will provide a rapid, qualitative indication of the paper abrasiveness when compared by experience to the relevant quantity of passing web.

To measure such linear quantities of web contact, a calibrated wheel 70 drive of 1 foot circumference, for a signal pulse generator 71 is secured to the pivot bracket 26, FIG. 1. Positional alignment of the wheel 70 provides surface drive contact with the turning roll 10 simultaneous with test contact of the specimen 60. Electrical pulses from the signal generator 71 actuate a digital counter and visual display not shown. To further regulate the bearing pressure of the calibrated wheel 70, the spindle thereof is resiliently suspended independently of the pivot bracket 26. This expedient addresses the accuracy and long-lived reliability of the instrument.

Engagement and disengagement control over the present invention may be entirely manual or automated as desired. In general, the operation sequence first requires air pressure admission to the horizontal shift motor 24 to extend the carriage and shoe assemblies into alignment with the web W. Upon such alignment, the lower cylinder 31 of vertical motor 30 is charged to swing the pivot bracket 26 and shoe assembly 40 into near proximity of the running web W. Final engagement of the test specimen with the web is motivated by a low pressure charge of the upper cylinder 33 portion of the vertical motor 30.

The pressure and volume distinction between upper and lower cylinders 33 and 31 provides distinctive spring rates in series along the column axis of motor 30. The low pressure of upper cylinder 33 translates a soft engagement force to the shoe 40 and test specimen 60. Simultaneously however, the small volume of the upper cylinder 33 provides high spring rate resilience to the contact force bias.

On a typical application, the lower cylinder 31 will be charged with approximately 60 psig whereas upper cylinder 33 will be charged with approximately 30 psig.

Relevant to the magnitude of contact pressure exerted by the upper cylinder 33 is the degree of self-energization as the phenomenon is known to the shoe brake art. Such self-energization is dictated, in-part, by the location of the pivot bracket 26 swing axis relative to the turning roll 10 axis and the arcuate contact angle of the test specimen 60. These parameters are normally distinctive to specific installations but are extremely important to the maintenance of correct specimen contact pressure.

Final engagement of the test specimen 60 with the web simultaneously engages the calibrated wheel 70 to record the linear quantity of web passing the specimen 60. Consequently, it is not necessary to precisely time the specimen contact with the web for calculation of the web contact length from known machine speeds which may vary greatly over an elapsed test interim.

An automatically controlled unit may be constructed to disengage the specimen 60 from the web upon arrival at a predetermined measured web length by reversal of the foregoing engagement sequence. Moreover, by connection of the unit control with the papermachine web-break alarm, a test interim started before a web break may be continued after web restoration. In this case, a controlled retraction sequence is initiated prior to completion of the set-point footage count. Because the previously accumulated footage count remains, however, the test engagement sequence is initiated upon termination of the web-break alarm. Accordingly, the test cycle is automatically restored until completion of the set-point footage count whereupon the test specimen is finally retracted from web engagement.

Figure 6:
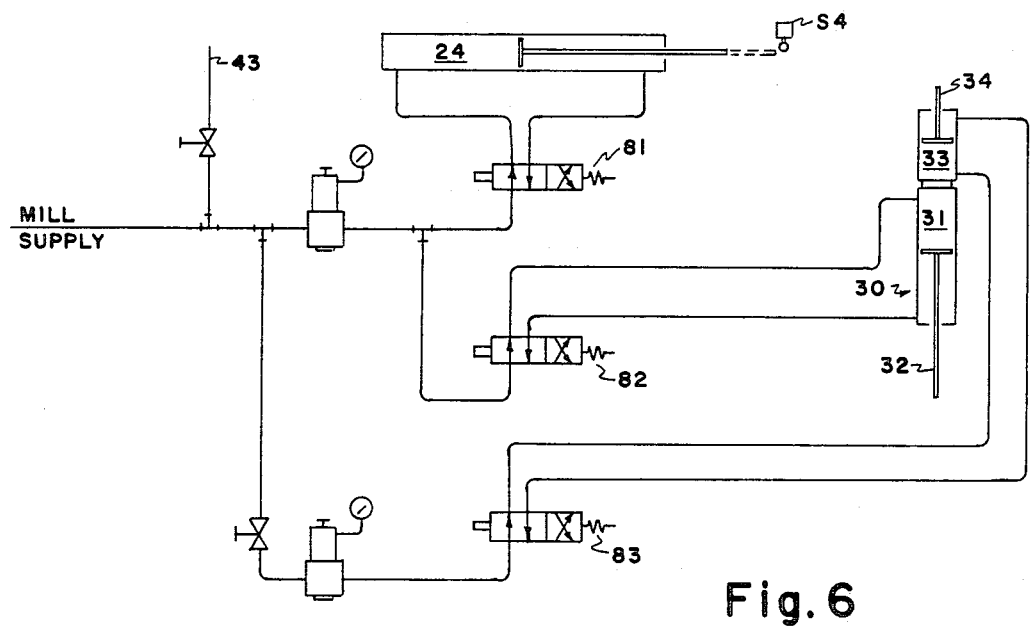
FIG. 6 is a schematic of the pneumatic control circuit.
Figure 7:
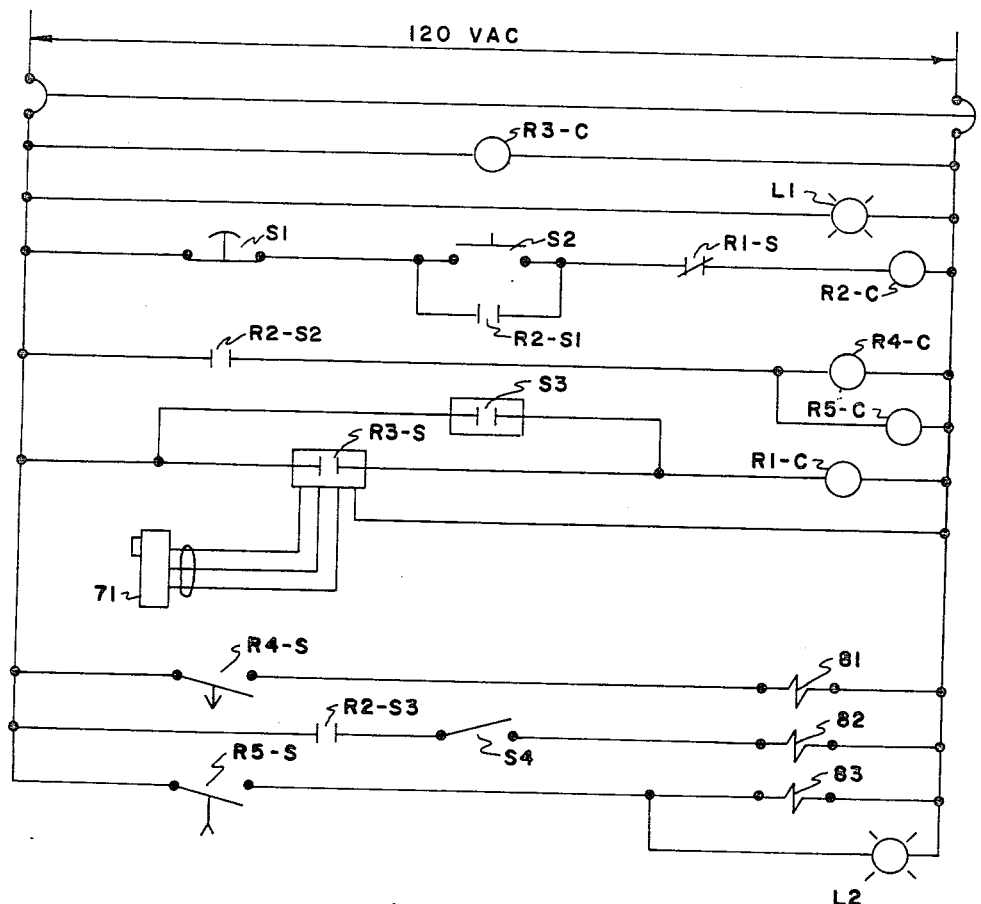
FIG. 7 is a schematic of the electric control circuit.

FIGS. 6 and 7 illustrate representative pneumatic and electronic control circuitry required to accomplish the aforedescribed functions.

Relative to FIG. 7, R3-C is an activation coil for prior art pulse counting logic R3-S which responds to signals from the calibrated wheel 70 pulse generator 71 to accumulate the summation of web length having passed the specimen 60 from the moment of engagement. Such accumulations are compared to a set-point value for initiation of other control signals upon correspondence between the set-point value and the accumulated value.

Components L1 and L2 are indicator lights to visually communicate that the unit power supply is energized (L1) and that the unit is operative (L2).

Start and stop switches S2 and S1 are normally open and closed respectively. When start switch S2 is closed, the coil R2-C of a 3-pole, double throw, normally open control relay is energized to close switches R2-S1, R2-S2 and R2-S3. Switch R2-S1 merely sustains power continuity across the N.O. start switch S2 after release of the starting contact pressure. Switch R2-S2 sustains continuity to the coils of time delay relays R4-C and R5-C. Similarly, switch R2-S3 sustains continuity to the control position limit-switch S4 located at the end of the horizontal fluid motor 24 engagement position stroke. Closure of limit switch S4 energizes control solenoid 82 to actuate the lower vertical motor 31.

Switch R1-S is a normally closed relay switch opened by energization of corresponding coil R1-C in circuit with counter control switch R3-S and the paper break switch S3.

Time delay relay switches R4-S and R5-S control actuation power to solenoids 81 and 83 to actuate the horizontal fluid motor 24 and upper vertical fluid motor 33, respectively.

The FIG. 7 electric control circuitry interfaces with the FIG. 6 pneumatic control schematic illustrating 4-way, solenoid actuated, control valves 81, 82 and 83 respective to the horizontal fluid motor 24, the lower cylinder 31 of the vertical motor 30 and the upper cylinder 33 of the vertical motor 30.

Specimen 60 preparation for a test requires no more than an accurate weighing of the specimen. Furthermore, since the test principal is predicated solely on the magnitude of specimen weight loss over a known web length, depending on the specimen material selected and the proportional weight loss over a test interim, a particular specimen may be used repeatedly over as many test cycles.

Upon determination of the specimen 60 weight loss, a web abrasiveness index may be developed as a function of the ratio between weight loss and web length. A partially normalized relationship of the measured parameters may take the form:

$$\text{Abrasion Index} = \frac{\text{Specimen wt. loss (lb)} \times 10^6 \text{ ft. web}}{\text{Abraded Specimen Area (ft.}^2) \times \text{web length used (ft.)}}$$

It will be recognized that the above relation does not include a bearing pressure parameter. For Index comparisons between abrasiveness tests made of different webs from the same machine and test instrument, bearing pressure may be assumed constant and therefore ignored in the index computation. However, if webs from different papermachines and test instruments are to be compared by a truly normalized index, it is imperative that the specimen bearing pressure be determined and considered in the Index calculation.

Specimen weighing is not the only technique whereby the present invention may be used. Another technique would involve a specimen 60 fabricated with multiple plated laminations of visually discernible layers similar to that of the copper clad brass technique previously described. By merely counting the number of abraded layers, each having a known thickness, over a standard web test length, a reasonably accurate indication of the web abrasiveness may be concluded.

Figure 8:
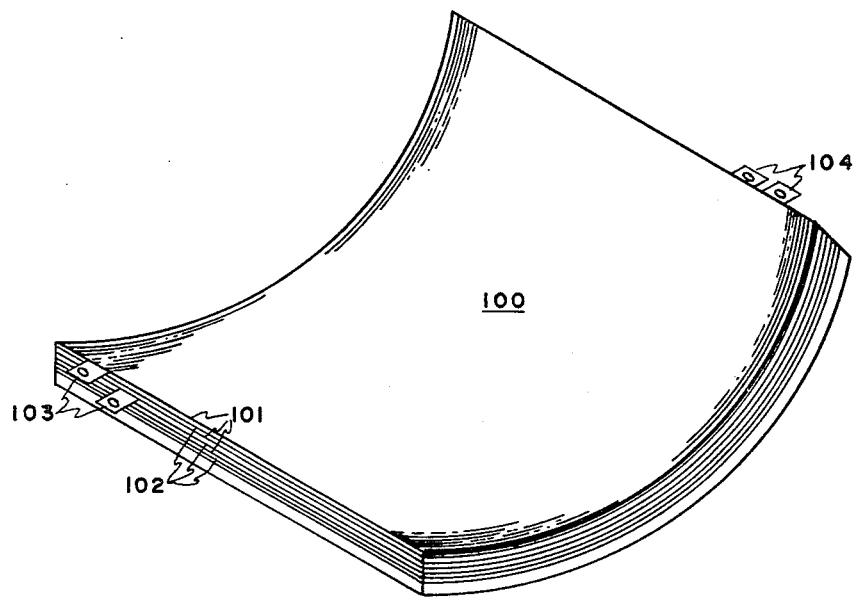
FIG. 8 is an alternative embodiment of a test specimen.

Another measurement technique exploitative of the present invention is represented by FIG. 8 wherein a composite specimen 100 is fabricated by laminating multiple layers of electrically conductive, soft metal foil 101 separated by layers of insulation paper 102. Each foil layer 101 is provided with connector tabs 103 and 104 on opposite ends of the specimen 100 for electrical continuity therebetween. As an abrasiveness test progresses electrical continuity across the foil layers will sequentially be interrupted to indicate the magnitude of material removal. By correlating the sequence of foil continuity interruption to the corresponding web length, conclusions may be drawn as to the abrasiveness of the web in-transit through the machine.

Having fully described my invention other modifications and use techniques may readily appear to those of ordinary skill in the art. As my invention, however,

I claim:

1. A method of determining the surface abrasiveness of a papermachine web comprising the steps of:
   A. Passing said web over an arcuate portion of a rotating web turning roll surface secured to a papermachine support frame;
   B. Weighing a sheet specimen of sacrificial material.
   C. Securing said specimen to a pressure shoe pivotally mounted to said support frame;
   D. Contacting said papermachine web along one lateral edge thereof with said weighed specimen within a substantially dry web zone in said papermachine radially opposite from said rotating web turning roll surface by pivoting the pressure shoe toward the turning roll wherein one sheet face of said specimen is concentrically arced with said turning roll and radially pressed against said web with a regulated bearing pressure;
   E. Running an incremental length of said web in contact with said specimen;

F. Measuring the length of said web increment simultaneous with the running thereof;

G. Disengaging said specimen from contact with said web at the end of said measured web increment; and, H. Weighing said disengaged specimen to determine the quantity of sacrificial material removed from said specimen per unit of web length.

2. A method of determining the surface abrasiveness of a papermachine web comprising the steps of:

A. Passing a substantially finished papermachine web over an arcuate portion of a rotating web turning roll surface secured to a papermachine support frame;

B. Securing a test specimen to a pressure shoe pivotally mounted to said support frame near one axial end of said turning roll, said test specimen comprising a laminated sheet having a plurality of visually discernible layers;

C. Pivoting said pressure shoe toward said turning roll to press said specimen into concentric arcuate contact and regulated bearing pressure against a surface of said web opposite from contact with said turning roll;

D. Measuring a length of papermachine web in passing contact with said test specimen;

E. Disengaging said test specimen from contact with said web at the end of said measured web length by pivoting said pressure shoe away from said turning roll; and, F. Coordinating said passing web length to the number of said test specimen layers exposed by web abrasion to conclude the relative abrasiveness of said web.

3. A method of determining the surface abrasiveness of a papermachine web comprising the steps of:

A. Passing a substantially finished papermachine web over an arcuate portion of a rotating web turning roll surface secured to a papermachine support frame;

B. Securing a test specimen to a pressure shoe pivotally mounted to said support frame near one axial end of said turning roll, said test specimen comprising a laminated strip of electrically conductive foil;

C. Monitoring the electrical continuity of said foil strip;

D. Pivoting said pressure shoe toward said turning roll to press said specimen into concentric arcuate contact and regulated bearing pressure against a surface of said web opposite from contact with said turning roll;

E. Measuring a length of papermachine web in passing contact with said test specimen;

F. Coordinating to a corresponding web length the continuity interruption of said roil strip of abrasive destruction to determine the relative abrasiveness of said web; and, G. Disengaging said test specimen from contact with said web by pivoting said pressure shoe away from said turning roll.

* * * * *

UNITED STATES PATENT OFFICE
CERTIFICATE OF CORRECTION

PATENT NO. : 4,253,913
DATED : March 3, 1981
INVENTOR(S) : Partha S. Chaudhuri

It is certified that error appears in the above-identified patent and that said Letters Patent are hereby corrected as shown below:

Column 8, line 25, (Claim 3, line 21) delete "roil" and insert therefor --foil--.

Signed and Sealed this

Twelfth Day of May 1981

[SEAL]

Attest:

RENE D. TEGTMEYER

Attesting Officer

Acting Commissioner of Patents and Trademarks